(12) United States Patent
Jiang et al.

(10) Patent No.: US 11,023,808 B1
(45) Date of Patent: Jun. 1, 2021

(54) SYSTEM AND METHOD OF MODELING VISUAL PERCEPTION V1 AREA

(71) Applicant: HRL LABORATORIES, LLC, Malibu, CA (US)

(72) Inventors: Qin Jiang, Park Oaks, CA (US); Narayan Srinivasa, Oak Park, CA (US)

(73) Assignee: HRL Laboratories, LLC, Malibu, CA (US)

(*) Notice: Subject to any disclaimer, the term of this patent is extended or adjusted under 35 U.S.C. 154(b) by 0 days.

(21) Appl. No.: 16/663,195

(22) Filed: Oct. 24, 2019

Related U.S. Application Data

(63) Continuation-in-part of application No. 15/141,733, filed on Apr. 28, 2016, now abandoned, which is a
(Continued)

(51) Int. Cl.
*G06N 3/08* (2006.01)
*G06K 9/62* (2006.01)
(Continued)

(52) U.S. Cl.
CPC ............ *G06N 3/082* (2013.01); *G06K 9/6256* (2013.01); *G06N 3/049* (2013.01); *G06N 3/0635* (2013.01)

(58) Field of Classification Search
None
See application file for complete search history.

(56) References Cited

U.S. PATENT DOCUMENTS

| | | | | |
|---|---|---|---|---|
| 5,136,687 | A * | 8/1992 | Edelman | G06N 3/04 706/20 |
| 2008/0091425 | A1 * | 4/2008 | Kane | G10L 17/04 704/246 |

(Continued)

OTHER PUBLICATIONS

NPL: "Stable learning of functional maps in self-organizing spiking neural networks with continuous synaptic plasticity", Srinivasa et al. (Year: 2013).*

(Continued)

*Primary Examiner* — Tracy C Chan
(74) *Attorney, Agent, or Firm* — Lewis Roca Rothgerber Christie, LLP

(57) ABSTRACT

A system to detect a feature in an input image comprising a processor to evaluate a model including: four layers including: a supragranular layer, a granular layer, a first infragranular layer, and a second infragranular layer, each of the layers including a base connection structure including: an excitatory layer including a excitatory neurons arranged in a two dimensional grid; and an inhibitory layer including a inhibitory neurons arranged in a two dimensional grid; within-layer connections between the neurons of each layer in accordance with a Gaussian distribution; between-layer connections between the neurons of different layers, the probability of a neuron of a first layer of the different layers to a neuron of a second layer of the different layers in accordance with a uniform distribution; and input connections from lateral geniculate nucleus (LGN) neurons of an
(Continued)

input LGN layer to the granular layer in accordance with a uniform distribution.

19 Claims, 10 Drawing Sheets
(3 of 10 Drawing Sheet(s) Filed in Color)

Related U.S. Application Data continuation-in-part of application No. 13/691,130, filed on Nov. 30, 2012.

(60) Provisional application No. 62/154,603, filed on Apr. 29, 2015.

(51) Int. Cl.
*G06N 3/063* (2006.01)
*G06N 3/04* (2006.01)

(56) References Cited

U.S. PATENT DOCUMENTS

| | | | | |
|---|---|---|---|---|
| 2010/0312730 | A1* | 12/2010 | Weng | G06N 3/08 706/15 |
| 2011/0035215 | A1* | 2/2011 | Sompolinsky | G10L 15/02 704/231 |
| 2014/0012789 | A1* | 1/2014 | Bazhenov | G06N 3/088 706/25 |
| 2014/0067740 | A1* | 3/2014 | Solari | G06N 3/008 706/27 |
| 2015/0269439 | A1* | 9/2015 | Versace | G06T 7/194 382/103 |
| 2017/0300788 | A1* | 10/2017 | Cao | G06K 9/6267 |

OTHER PUBLICATIONS

NPL "Integration of nanoscale memristor synapses in neuromorphic computing architectures" Indiveri et al. (Year: 2013).*
Choe et al. "Self-organization and segmentation in a laterally connected orientation map of spiking neurons", Neuro computing (1998), pp. 139-157 (Year: 1998).*
Nere et al. "A Neuromorphic Architecture for Object Recognition and Motion Anticipation Using Burst-STDP" (Year: 2012).*
Bartsch et al. "Combined Hebbian development of geniculocortical and lateral connectivity in a model of primary visual cortex" (Year: 2001).*
Cai "An effective kinetic representation of fluctuation-driven neuronal networks with application to simple and comples cells in visual cortex" (Year: 2004).*
Bartsch, A.P. et al. "Combined Hebbian development of geniculocortical and lateral connectivity in a model of primary visual cortex," *Biological Cybernetics, Springer-Verlag*, No. 84, pp. 41-55 (2001).
Cruz-Albrecht, J.M., et al. "A scalable neural chip with synaptic electronics using CMOS integrated memristors" Nanotechnology 24 384011 (2013), 11 pages.

* cited by examiner

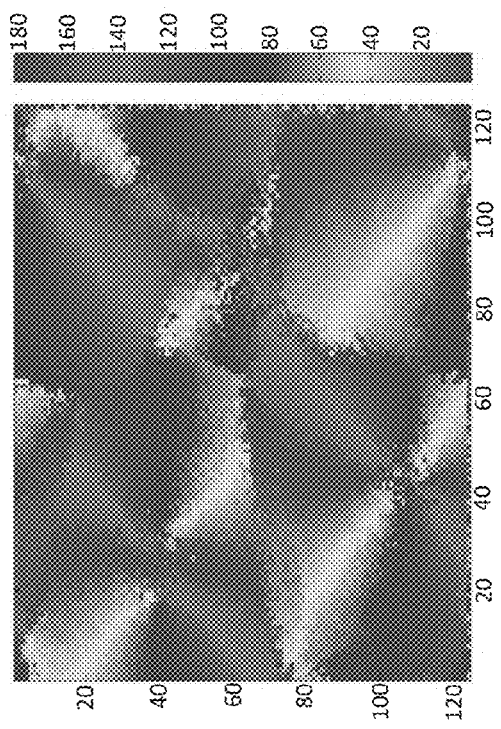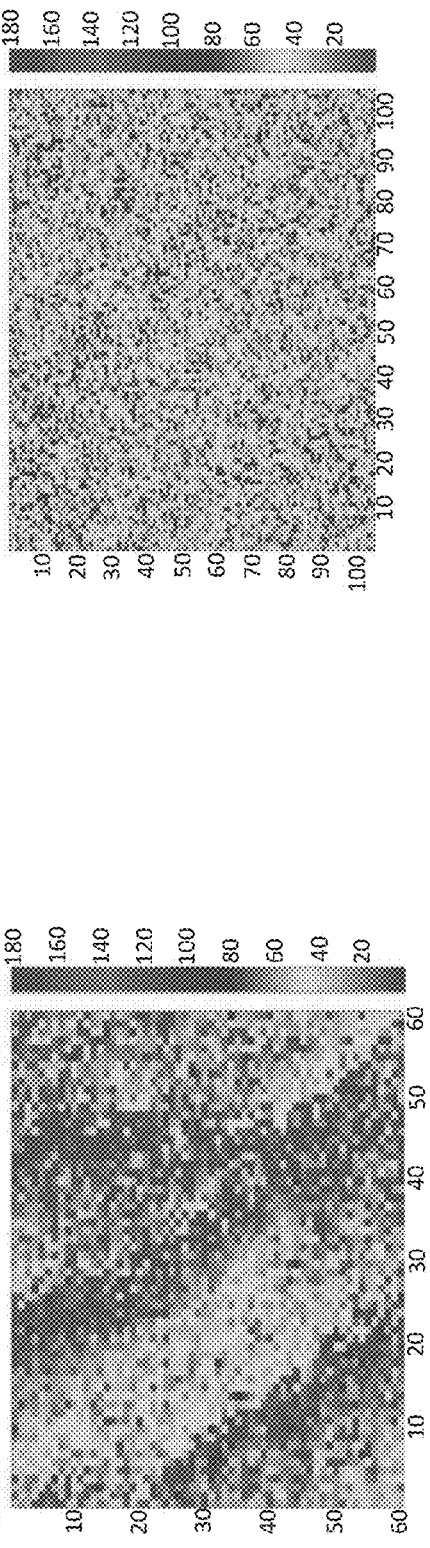
FIG.6A LAYER 3
FIG.6B LAYER 4
FIG.6C LAYER 5
FIG.6D LAYER 6

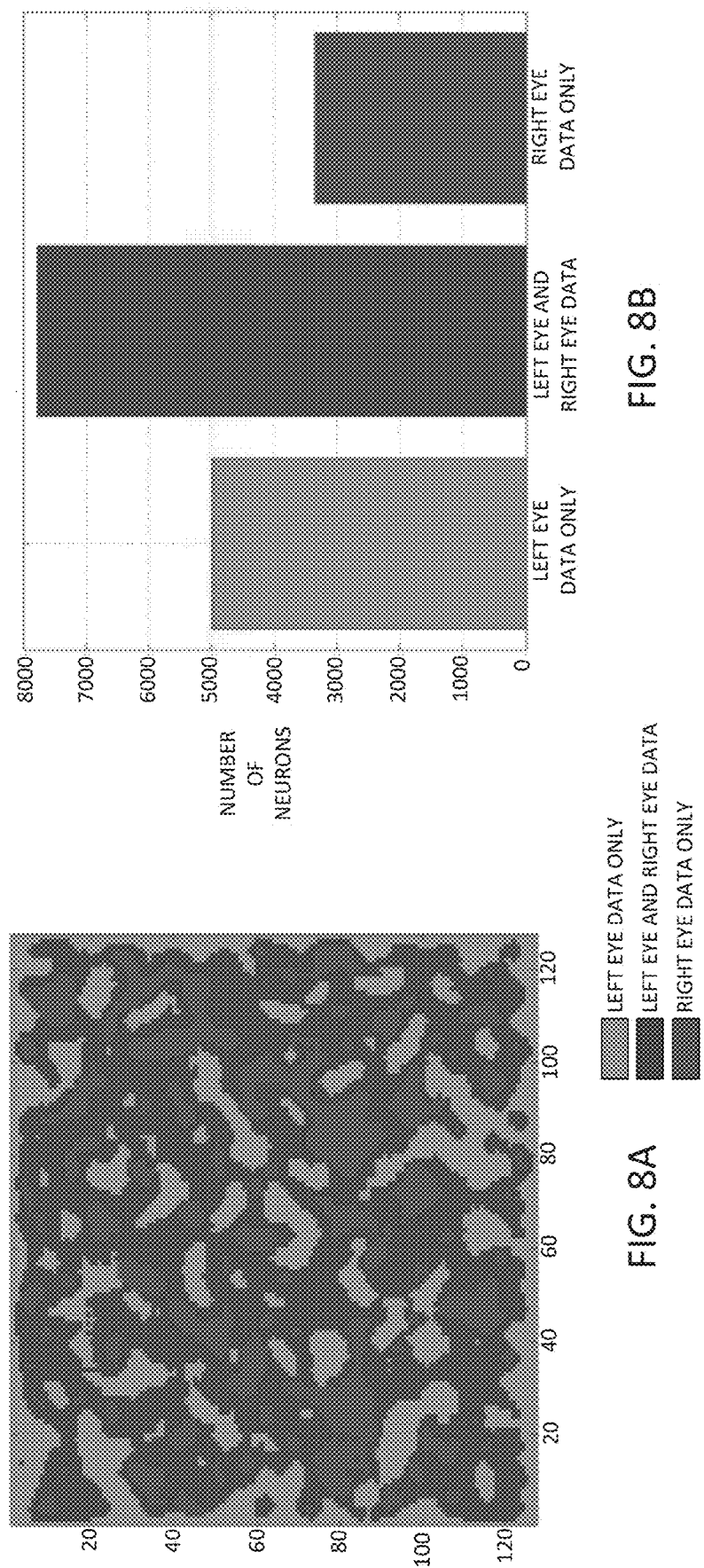

SYSTEM AND METHOD OF MODELING VISUAL PERCEPTION V1 AREA

CROSS-REFERENCE TO RELATED APPLICATION

This application is a continuation-in-part of U.S. patent application Ser. No. 13/691,130, "A Method of Modeling Functions of Orientation and Adaptation on Visual Cortex," filed Nov. 30, 2012, the entire disclosure of which is incorporated by reference herein, and this application is a continuation-in-part of U.S. patent application Ser. No. 15/141,733, "A System and Method of Modeling Visual Perception V1 Area" filed Apr. 28, 2016, the entire disclosure of which is incorporated by reference herein, which claims priority to and the benefit of U.S. Provisional Patent Application No. 62/154,603, "A Method of Modeling Visual Perception V1 Area," filed in the United States Patent and Trademark Office on Apr. 29, 2015 the entire disclosure of which is incorporated by reference herein.

STATEMENT REGARDING FEDERALLY SPONSORED RESEARCH OR DEVELOPMENT

The present invention was made with support from the United States Government under Contract No. HR0011-09-C-0001 awarded by the Defense Advanced Research Project Agency (DARPA). The United States Government has certain rights in this invention.

BACKGROUND

1. Field

Aspects of embodiments of the present invention are related to methods for modeling the V1 visual perception area of a brain and automated systems implementing corresponding models to recognize features in images.

2. Related Art

The automated detection of features and objects in images is an area of interest in computer vision, as these detection techniques can be used to track moving objects and to recognize particular shapes.

In the human visual system, the primary visual cortex V1 plays a major part in the sensing of visual information. Prior work in computer vision has attempted to simulate the behavior of V1 using artificial visual processing systems that are modeled on the anatomical pathways and four functional layers (Layer 2/3, Layer 4, Layer 5, and Layer 6) of V1, as identified in biological studies (see, e.g., Bartsch, A. P. and van Hemmen, J. L. "Combined Hebbian development of geniculocortical and lateral connectivity in a model of primary visual cortex," *Biological Cybernetics*, Springer-Verlag, no. 84, pp. 41-55 (2001)), the entire disclosure of which is incorporated herein by reference. In addition, prior computational models and simulation systems have simulated Layer 4 of V1 (e.g., U.S. patent application Ser. No. 13/691,130, titled "A Method of Modeling Functions of Orientation and Adaptation on Visual Cortex" filed in the United States Patent and Trademark Office on Nov. 30, 2012, the entire disclosure of which is incorporated herein by reference). However, many details regarding the processing of visual signals within the primary visual cortex V1 remain unknown, thereby making it difficult to create accurate and performant models.

SUMMARY

Aspects of embodiments of the present invention are directed to systems and methods for computationally modeling and emulating the function of the four layers (Layer 2/3, Layer 4, Layer 5, and Layer 6) of the primary visual cortex V1. These aspects of the present invention include: 1) a computation structure to construct the four layers of the V1 network; 2) a system to emulate the primary visual cortex V1; and 3) a method for emulating the lateral geniculate nucleus (LGN) layer and retinal waveform. Simulating or emulating the primary visual cortex system V1 and comparing data observed in vivo with the results of the emulation while varying parameters of the model can provide insight into the biological structures and can also suggest ways to improve computer vision systems. As such, the computational models and computing structures according to aspects of the present invention can be used to develop more advanced visual information processing systems that are similar to the human visual system, thereby improving performance of artificial computer vision systems.

The emulated V1 network constructed using computational models and computing structures according to embodiments of the present invention is able to produce V1 functionalities including an ocular dominance map (ODM) and a synaptic conductance distribution map (CDM) that are similar to those obtained from biological experiments.

According to one embodiment of the present invention, a method for emulating a primary visual cortex using a model, the model including: four layers including: a supragranular layer, a granular layer, a first infragranular layer, and a second infragranular layer, each of the four layers including a base connection structure, the base connection structure including a plurality of layers including: an excitatory layer including a plurality of excitatory neurons arranged in a two dimensional grid; and an inhibitory layer including a plurality of inhibitory neurons arranged in a two dimensional grid; a plurality of within-layer connections between the neurons of each layer, the probability of a first neuron of the layer being connected to a second neuron of the same layer being a function of the distance between the first neuron and the second neuron in accordance with a Gaussian distribution; a plurality of between-layer connections between the neurons of different layers, the probability of a neuron of a first layer of the different layers to a neuron of a second layer of the different layers in accordance with a uniform distribution; and a plurality of input connections from a plurality of lateral geniculate nucleus (LGN) neurons of an input LGN layer to the Layer 4, the probability of an LGN neuron being connected to a neuron of the Layer 4 being in accordance with a uniform distribution, the method including: supplying an input signal from an image sensor to the LGN neurons; measuring an output activation of neurons in the four layers to detect the presence of at least one feature in the input signal; and outputting the output activation of neurons in the four layers.

A plurality of model parameters may include a plurality of connection ratios, each of the connection ratios corresponding to the uniform distribution associated with a plurality of between-layer connections between a first layer of the different layers to a second layer of the different layers.

A plurality of model parameters may include a plurality of Gaussian distribution parameters A and σ for each of the plurality of layers, wherein the first neuron of the layer is located at coordinates $(x_0, y_0)$ within the layer and the second neuron of the layer is located at coordinates $(x, y)$ within the layer, and wherein the probability P that the first neuron is connected to the second neuron is:

$$P(x, y) = A * e^{\frac{-[(x-x_0)^2 + (y-y_0)^2]}{2\sigma}}$$

A plurality of model parameters may include a plurality of neuron populations, wherein each of the neuron populations corresponds to the number of neurons in a corresponding one of the layers.

The model may be trained by: setting a plurality of initial synaptic weights, each of the initial synaptic weights corresponding to one of the connections; generating visual stimulus signals; supplying the visual stimulus signals to the LGN neurons; and updating the synaptic weights of the connections by iteratively: computing propagating signals through the connections in accordance with the synaptic weights; determining whether each neuron releases a signal in accordance with an accumulated signal; determining a plurality of timings of the signals released by the neurons; and computing new synaptic weights in accordance with the timings and spike timing dependent plasticity synaptic learning.

The model may further be trained by supplying a plurality of background random signals to the neurons.

The generating the visual stimulus signals may include generating a plurality of spiking sequences.

The method may further include analyzing the synaptic weights to generate an ocular dominance map and a synaptic conductance distribution map.

The visual stimulus signals may include a plurality of left visual stimulus signals and a plurality of right visual stimulus signals, wherein the LGN neurons include a plurality of left LGN neurons configured to receive the left visual stimulus signals and plurality of right visual stimulus signals configured to receive the right visual stimulus signals, and wherein each of the neurons in the excitatory layer of Layer 4 is connected with non-zero synaptic weight to only left LGN neurons or to only right LGN neurons.

The method may further include: supplying an input signal from an image sensor to the LGN neurons; and measuring an output activation of neurons in the four layers.

The processor may be a neuromorphic chip.

According to one embodiment of the present invention, a system configured to detect a feature in an input image includes a processor configured to evaluate a model, the model being configured based on a plurality of model parameters, the model including: four layers including: Layer 2/3, Layer 4, Layer 5, and Layer 6, each of the four layers including a base connection structure, the base connection structure including a plurality of layers including: an excitatory layer including a plurality of excitatory neurons arranged in a two dimensional grid; and an inhibitory layer including a plurality of inhibitory neurons arranged in a two dimensional grid; a plurality of within-layer connections between the neurons of each layer, the probability of a first neuron of the layer being connected to a second neuron of the same layer being a function of the distance between the first neuron and the second neuron in accordance with a Gaussian distribution; a plurality of between-layer connections between the neurons of different layers, the probability of a neuron of a first layer of the different layers to a neuron of a second layer of the different layers in accordance with a uniform distribution; and a plurality of input connections from a plurality of lateral geniculate nucleus (LGN) neurons of an input LGN layer to the Layer 4, the probability of an LGN neuron being connected to a neuron of the Layer 4 being in accordance with a uniform distribution; the system being configured to: receive input image data from an image sensor; supply the input image data to the LGN neurons of the model; compute an activation output of the model; and generate user feedback in accordance with the activation output of the model, the user feedback indicating the presence of the feature in the input data.

The model parameters may include a plurality of connection ratios, each of the connection ratios corresponding to the uniform distribution associated with a plurality of between-layer connections between a first layer of the different layers to a second layer of the different layers.

The model parameters may include a plurality of Gaussian distribution parameters A and σ for each of the plurality of layers, wherein the first neuron of the layer is located at coordinates $(x_0, y_0)$ within the layer and the second neuron of the layer is located at coordinates (x, y) within the layer, and wherein the probability P that the first neuron is connected to the second neuron is:

$$P(x, y) = A * e^{\frac{-[(x-x_0)^2 + (y-y_0)^2]}{2\sigma}}$$

The model parameters may include a plurality of neuron populations, wherein each of the neuron populations corresponds to the number of neurons in a corresponding one of the layers.

The model parameters may further include a plurality of initial synaptic weights, each of the initial synaptic weights corresponding to one of the connections, and wherein the processor is configured to train the model by: receiving visual stimulus signals; supplying the visual stimulus signals to the LGN neurons; and updating the synaptic weights of the connections by iteratively: computing propagating signals through the connections in accordance with the synaptic weights; determining whether each neuron releases a signal in accordance with an accumulated signal; determining a plurality of timings of the signals released by the neurons; and computing new synaptic weights in accordance with the timings and spike timing dependent plasticity synaptic learning.

The processor may be further configured to train the model by supplying a plurality of background random signals to the neurons.

The visual stimulus signals may include a plurality of left visual stimulus signals and a plurality of right visual stimulus signals, wherein the LGN neurons include a plurality of left LGN neurons configured to receive the left visual stimulus signals and plurality of right visual stimulus signals configured to receive the right visual stimulus signals, and wherein each of the neurons in the excitatory layer of Layer 4 is connected with non-zero synaptic weight to only left LGN neurons or to only right LGN neurons.

The processor may be configured to: supply an input signal from an image sensor to the LGN neurons; and measure an output activation of neurons in the four layers.

The processor may be a neuromorphic chip.

According to one embodiment of the present invention, a non-transitory computer readable medium having instructions stored thereon that, when executed by a processor, cause the processor to: evaluate a model of a primary visual cortex, the model comprising: four layers comprising: a supragranular layer, a granular layer, a first infragranular layer, and a second infragranular layer, each of the four layers comprising a base connection structure, the base connection structure comprising a plurality of layers including: an excitatory layer comprising a plurality of excitatory neurons arranged in a two dimensional grid; and an inhibitory layer comprising a plurality of inhibitory neurons arranged in a two dimensional grid; a plurality of within-layer connections between the neurons of each layer, the probability of a first neuron of the layer being connected to a second neuron of the same layer being a function of the distance between the first neuron and the second neuron in accordance with a Gaussian distribution; a plurality of between-layer connections between the neurons of different layers, the probability of a neuron of a first layer of the different layers to a neuron of a second layer of the different layers in accordance with a uniform distribution; and a plurality of input connections from a plurality of lateral geniculate nucleus (LGN) neurons of an input LGN layer to the granular layer, the probability of an LGN neuron being connected to a neuron of the granular layer being in accordance with a uniform distribution; supply an input signal from an image sensor to the LGN neurons; measure an output activation of neurons in the four layers to detect the presence of at least one feature in the input signal; and output the output activation of neurons in the four layers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, together with the specification, illustrate exemplary embodiments of the present invention, and, together with the description, serve to explain the principles of the present invention.

FIGS. 6A-6D are depictions of the conductance distribution maps experimentally obtained from the E-layers of the four layers of the model of V1—Layer 2/3, Layer 4, Layer 5, and Layer 6, respectively after a training process according to one embodiment of the present invention.

FIG. 8A is an ocular dominance map of an initial V1 network, before running the training process, according to one embodiment of the present invention.

FIG. 8B is a histogram illustrating the ocular dominance of neurons in the initial V1 network, before running the training, according to one embodiment of the present invention.

DETAILED DESCRIPTION

Figure 1:
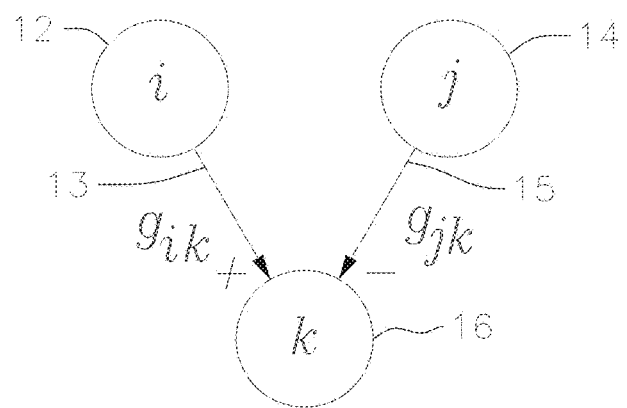
FIG. 1 is a schematic illustration of connection between three neurons according to one embodiment of the present invention.

In the following detailed description, only certain exemplary embodiments of the present invention are shown and described, by way of illustration. As those skilled in the art would recognize, the invention may be embodied in many different forms and should not be construed as being limited to the embodiments set forth herein. Like reference numerals designate like elements throughout the specification.

Aspects of embodiments of the present invention are directed to systems and methods for emulating the four layers of the primary visual cortex V1 at a spiking neuron level in order to emulate the full functionalities of V1. The four layers include: Layer 2/3 or supragranular layer, which contain small and medium-size pyramidal neurons; Layer 4 or granular layer, which contains stellate and pyramidal neurons; Layer 5 or first infragranular layer, which contains large pyramidal neurons; and Layer 6 or second infragranular layer, which contains large pyramidal neurons and spindle-like pyramidal and multiform neurons.

The human visual system is a powerful visual information sensing system. Fully understanding the human visual system is an important area of research in biology and may have significant applications in computer vision. The primary visual cortex of the human visual system, called V1, plays a major role in visual information sensing and V1 is a heavily studied area of the visual cortex in biology, anatomy, and neuroscience. Nevertheless, biological studies of the primary visual cortex V1 have not yet revealed how it processes visual signals. Therefore, computational models and systems emulating the primary visual cortex system V1 can be very useful for understanding visual signal processing inside the human visual cortex and for implementing these processing capabilities in computer vision systems.

Biological studies of the anatomy of the visual system have shown that V1 can be divided into six functional layers, four of which contain a large number of neurons that play major roles in visual signal processing. The four layers are known as Layer 2/3 (or supragranular layer), Layer 4 (or granular layer), Layer 5 (or first infragranular layer), and Layer 6 (or second infragranular layer). Among these layers, Layer 4 receives the most visual signals (information) from the lateral geniculate nucleus (LGN), which is one of the visual sensing areas in the visual cortex.

Aspects of embodiments of the present invention are directed to modeling techniques to model the four layers of V1 and a system to emulate the V1 model. In addition, aspects of embodiments of the present invention are directed to methods for modeling retinal waveforms and the LGN layer. To validate the models and system, emulation is performed by supplying input data to the models and iteratively updating the weights of connections between the modeled neurons. After running the emulated model for a number of time iterations (or cycles), the weights of the connections may settle into stable values. The resulting weights of the connections may be interpreted as output neuron conductance distribution maps (or orientation maps) and ocular dominance maps. The emulation results show that the resulting neuron conductance distribution maps and ocular dominance maps are consistent with neuron conductance distribution maps and ocular dominance maps found in biological organisms, thereby validating the underlying model described herein. As such, embodiments of the present invention may provide useful systems for detecting visual objects (e.g., objects in an image).

Modeling the Four Layers of V1

The primary visual cortex V1 includes four functional layers made up of millions of neurons. Embodiments of the present invention model the four layers based on a model of single neurons interacting with each other in a network. Because the four layers share a similar anatomic structure, a base structure is used as a building block for the four layer network.

In each of the four modeled layers of V1, each neuron receives signals from other neurons. The received electronic signals are accumulated inside the neuron and, when the accumulated signal reaches a threshold level, the neuron releases a firing spike (or neuron firing), which is transmitted to other neurons. In some embodiments of the present invention, the neuron firing of a single neuron can be modeled as a leaky integrate-and-fire model described by the dynamic equation of a neuron membrane potential and current, as given in Equation 1 below:

$$\tau_m \frac{du(t)}{dt} = -u(t) + RI(t) \quad (1)$$

where $u(t)$ is the membrane potential, $I(t)$ is the membrane current, and the constants $\tau_m$ and $R$ are the membrane time constant and resistance of the neuron, respectively.

In one embodiment of the present invention, when the membrane potential of a modeled neuron crosses a threshold value, the neuron releases a spiking signal to other neurons. Broadly speaking, the neuron may be classified as an inhibitory (I) neuron or an excitatory (E) neuron. An inhibitory neuron releases inhibitory signals, which causes a decrease in the neuron firing on its target neurons (e.g., a decrease in the signal) while an excitatory neuron releases excitatory synaptic signals, which cause an increase in neuron firing on its target neurons (e.g., an increase in the signal).

FIG. 1 is an illustration of three neurons, where neuron i 12 and neuron j 14 transmit signals along connections 13 and 15 to the same target neuron k 16. In the example shown, neuron i 12 is an excitatory neuron and neuron j 14 is an inhibitory neuron. As such, the membrane potential of neuron k 16 can be written as:

$$u_k(t) = \varepsilon_{ik}(t) + \varepsilon_{jk}(t) \quad (2)$$

where:

$$\varepsilon_{ik}(t) = u_0 \left[ 1.0 - e^{\frac{-(t-t^f)}{\tau_{ik}}} \right]$$

and

-continued $$\varepsilon_{jk}(t) = u_0 \left[ e^{\frac{-(t-t^f)}{\tau_{jk}}} - 1.0 \right]$$

and where the variable $u_0$ is initial membrane potential and $\tau_{ik}$ and $\tau_{jk}$ are membrane constants, and $t^f$ is neuron firing time. The component $\varepsilon_{ik}(t)$ is the contribution from the neuron i 12 and the component $\varepsilon_{jk}(t)$ is the contribution from the neuron j 14. For $t \geq t^f$, $\varepsilon_{ik}(t) \geq 0.0$ and therefore, the neuron i 12 is called an excitatory neuron for neuron k 16 (as such, the connection 13 from neuron j 12 to neuron k 16 is labeled with a "+"). Similarly, $t \geq t^f$, $\varepsilon_{jk}(t) \leq 0.0$ and therefore the neuron j 14 is called an inhibitory neuron for the neuron k 16 (as such, the connection 15 from neuron j 14 to neuron k 16 is labeled with a "−"). The four layers of V1 contain both excitatory neurons and inhibitory neurons.

According to the models according to embodiments of the present invention, the neurons are connected to each other through connections having synaptic weights. The synaptic weights play a role in neuron interaction and neuron group behavior and these weights can be developed based on synaptic learning rules. According to one embodiment of the present invention, the model develops the synaptic weights based on the learning rule of spike timing-dependent plasticity (STDP). In STDP learning, if $t_{pre}$ and $t_{post}$ are the spiking times for a pre-synaptic spike and a post-synaptic spike, respectively, the corresponding synaptic weight (or synaptic conductance g) is computed based on Equations 3, 4, and 5 below:

$$g_{new} = g_{old} + \Delta g \quad (3)$$

and $$\Delta g = g_{max} * F(\Delta t) \quad (4)$$

with $$F(\Delta t) = \begin{cases} A_+ * e^{\frac{\Delta t}{\tau_+}} & \text{if } \Delta t < 0 \\ -A_- * e^{\frac{\Delta t}{\tau_-}} & \text{if } \Delta t \geq 0 \end{cases} \quad (5)$$

where $\Delta t = t_{pre} - t_{post}$. As shown in FIG. 1, connection 13 from neuron i 12 to neuron k 16 has synaptic conductance $g_{ik}$, and connection 15 from neuron j 14 to neuron k 16 has synaptic conductance $g_{jk}$.

The constants $A_+$ and $A_-$ determine the maximum amount of synaptic modification. The time constants $\tau_+$ and $\tau_-$ determine the ranges of pre- to post-synaptic spike intervals. Generally, the STDP learning rule is that if a pre-synaptic spike can immediately generate a post-synaptic spike, then the synaptic weight is increased; otherwise, it is decreased. As a result, two neurons that are coupled together with a high synaptic weight means that the two neurons are closely coupled and are acting together. On the other hand, if two neurons are coupled with a low synaptic weight, then the activities of two neurons have little impact on one another. The learning process is a self-organization process of the network. In one embodiment, initially, all of the synaptic weights are set to zeros or very small values such as 0.01. When input waveforms are iteratively presented to the system, the neurons will generate synaptic spikes and synaptic spiking activity propagates from input LGN layer to the V1 network; the spiking activities in the network modify the synaptic weights by the STDP learning rule.

Figure 2:
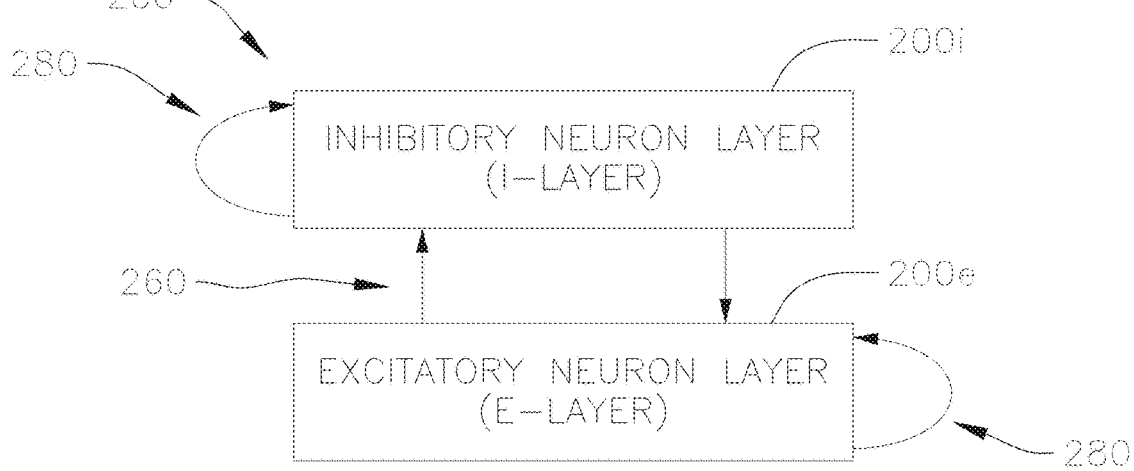
FIG. 2 is a schematic diagram illustrating the anatomical structure of a single layer of V1 in a model according to one embodiment of the present invention.

The four layers of V1 share a similar anatomical structure. FIG. 2 is a schematic diagram illustrating the anatomical structure 200 of a single layer of V1 in a model according to one embodiment of the present invention, where the layer of V1 includes one excitatory neuron layer (E-layer) 200e and one inhibitory neuron layer (I-layer) 200i and between-layer neural connections 260 connecting the layers to one another and within-layer neural connections 280 connecting the neurons within each layer (as used herein, a "between-layer neural connection" refers to a neural connection between two neurons in different layers, and a "within-layer neural connection" refers to a neural connection between two neurons in the same layer). In the model according to one embodiment of the present invention, the neurons in each layer are arranged on a two dimensional plane, with each neuron being located at unique coordinates (x, y) within the plane.

As shown in FIG. 2, according to one embodiment of the present invention, within each of the inhibitory neuron layer and the excitatory neuron layer, each neuron is modeled as being connected to neurons in its neighborhood (within-layer connections 280) according to a Gaussian-distributed connection. Each neuron is connected to other neurons within the same layer with a probability determined by Equation 6 below:

$$P(x, y) = A * e^{\frac{-[(x - x_0)^2 + (y - y_0)^2]}{2\sigma}} \quad (6)$$

where the coordinate $(x_0, y_0)$ is the location of the neuron and $(x, y)$ is the location of the neighbor neuron, and $P(x, y)$ is the probability that the neuron at $(x_0, y_0)$ is connected to the neuron at $(x, y)$. The constants A and σ determine the shape of the Gaussian distribution.

In addition, the neurons in each layer are connected to neurons in the other layer (between-layer connections 260). According to one embodiment of the present invention, the between-layer connection is modeled by a uniform distribution, where each neuron is connected to neurons in the other layer with a probability computed by:

$$P(x,y)=\text{Uniform}(0,1) \quad (7)$$

The neurons in the other layer are distributed in the entire layer.

The different layers (e.g., the inhibitory layer 200i and the excitatory layer 200e) may have different sizes. Therefore, finding corresponding neuron locations between two layers of different sizes may not be possible, thereby making it difficult to form Gaussian distributed connections. On the other hand, there is some biological evidence that uniformly-distributed connections exist in natural neuron connections.

Figure 3:
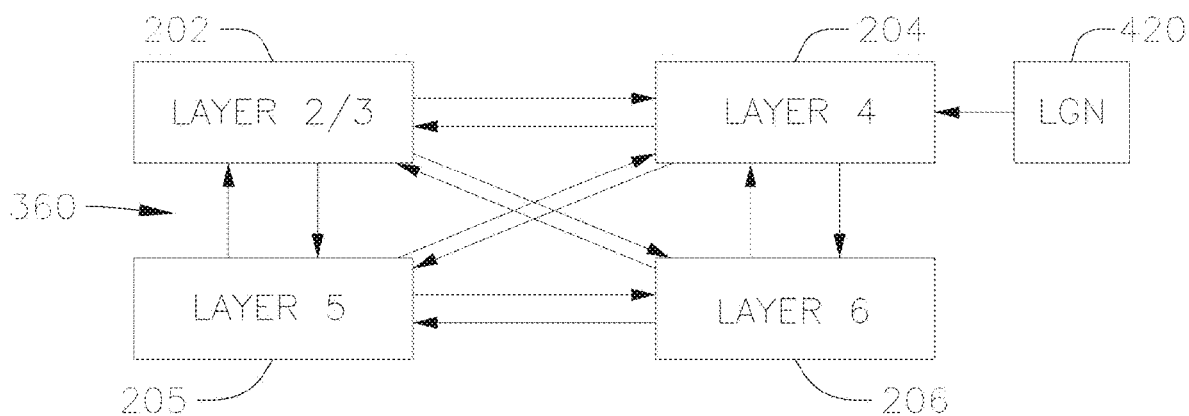
FIG. 3 is a schematic diagram illustrating the connections between the layers in the model of V1 according to one embodiment of the present invention.

Given the above base neural connection structure, in models according to some embodiments of the present invention, each layer of the four layers of V1 (Layer 2/3, Layer 4, Layer 5, and Layer 6) is modeled by substantially the same base connection structure. The layers differ in the sizes of the base connection structures and the ratios of the neural connections (or "connection ratios"). FIG. 3 is a schematic diagram illustrating the connections between the layers in the model 300 of V1 according to one embodiment of the present invention, where every layer is connected to each of the other three layers, and where input signals from the LGN are supplied to Layer 4. As shown in FIG. 3, the model 300 includes Layer 2/3 202, Layer 4 204, Layer 5 205, and Layer 6 206, each of which has a substantially similar base structure 200, although the number of neurons and connections may differ in each layer.

The neural connections 360 between the layers of V1 are all uniformly-distributed connections at particular connection ratios between the layers. In one embodiment, the connection ratio between two neural layers is determined based on biological experiments conducted in neuroscience. For example, an excitatory neuron in Layer 4 may be connected to the entire E-layer of Layer 2/3 202 at a particular corresponding connection ratio (e.g., a predetermined connection ratio) and may also be connected to the entire I-layer of Layer 2/3 at a different particular corresponding connection ratio.

Modeling the LGN Layer

Figure 4:
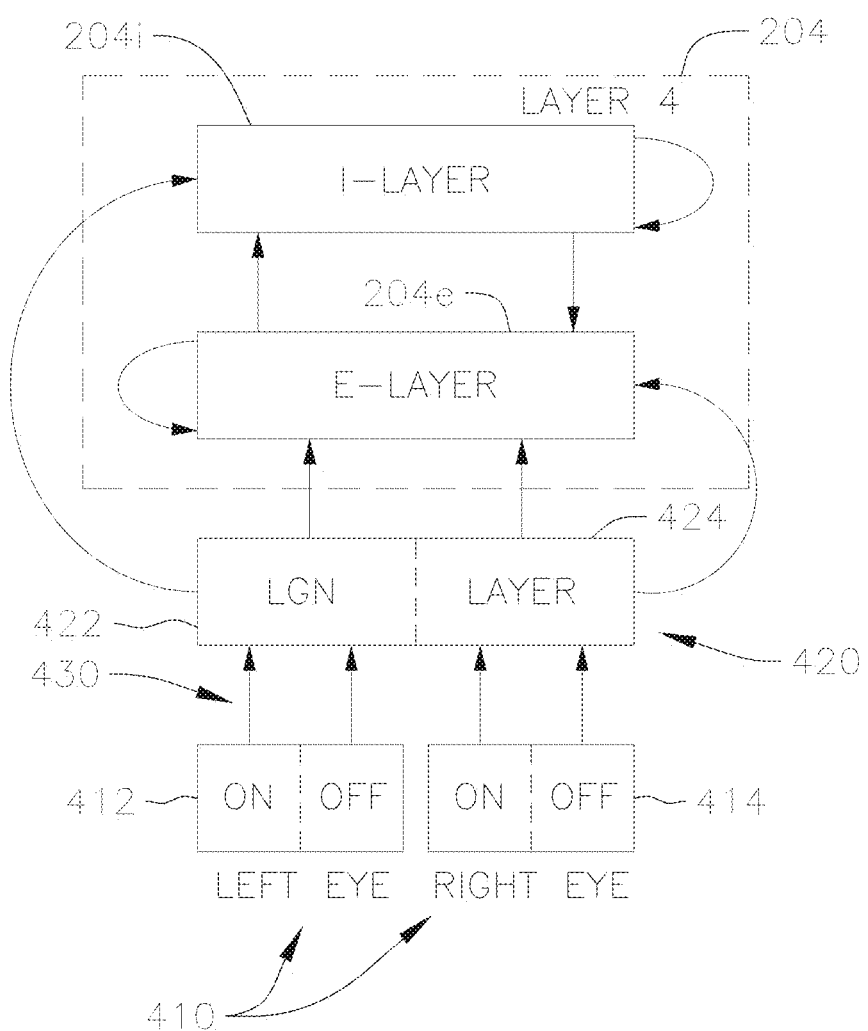
FIG. 4 is a schematic diagram illustrating connections between a lateral geniculate nucleus (LGN) layer, Layer 4, and input according to one embodiment of the present invention.

FIG. 4 is a schematic diagram illustrating connections between an LGN layer 420, Layer 4 204, and input 410 according to one embodiment of the present invention. The input 410 may include a left eye input 412 (e.g., left eye data from a training set or data from a first image sensor) and a right eye input 414 (e.g., right eye data from a training set or data from a second image sensor). As shown in FIG. 4, Layer 4 204 receives input signals from the LGN layer 402. According to one embodiment of the present invention, the LGN layer 402 is modeled as a layer of only excitatory neurons (E-neurons) and may be divided into two parts: a left part 422 connected to the left eye input 412 and a right part 424 connected to the right eye input 414. (In some embodiments of the present invention, a monocular vision system is modeled, in which case the LGN layer 420 is not divided into a left eye input and a right eye input.)

According to one embodiment of the present invention, connections 430 between the LGN layer 420 and the input 410 are made with one-to-one connections. As a result, half of the LGN layer 422 is connected to the left-eye input 412 and the other half 424 is connected to the right-eye input 414. According to one embodiment, the connections from the LGN layer 420 to the E-layer 204e and I-layer 204i of Layer 4 204 are modeled as a uniformly distributed set of connections, e.g., each neuron in the LGN is uniformly connected to the entire E-layer 204e and I-layer 204i of Layer 4 204 at a particular connection ratio such as the connection ratios shown in Table 2 below. In one embodiment, the left eye and right eye inputs 412 and 414 receive images containing spiking amplitudes at each pixel location (e.g., 2D spiking sequences with Poisson distributions), known as "spiking images."

Emulation System

FIG. 5 is a flowchart illustrating a method for emulating a primary visual cortex V1 according to one embodiment of the present invention. The emulation may be performed using a computer system including a processor and memory storing instructions that implement the emulation method described below. However, embodiments of the present invention are not limited thereto and may be implemented using other computing devices such as a field programmable gate array (FPGA) or an application specific integrated circuit (ASIC).

For example, according to some embodiments of the present invention, the model is implemented on a hardware neuromorphic chip such as the chips developed as part of the DARPA-supported Systems of Neuromorphic Adaptive Plastic Scalable Electronics (SyNAPSE) program (see, e.g., Cruz-Albrecht, J. M., Derosier, T., and Srinivasa, N. "A scalable neural chip with synaptic electronics using CMOS integrated memristors." 2013 Nanotechnology 24 384011, the entire disclosure of which is incorporated herein by reference).

Figure 5A:
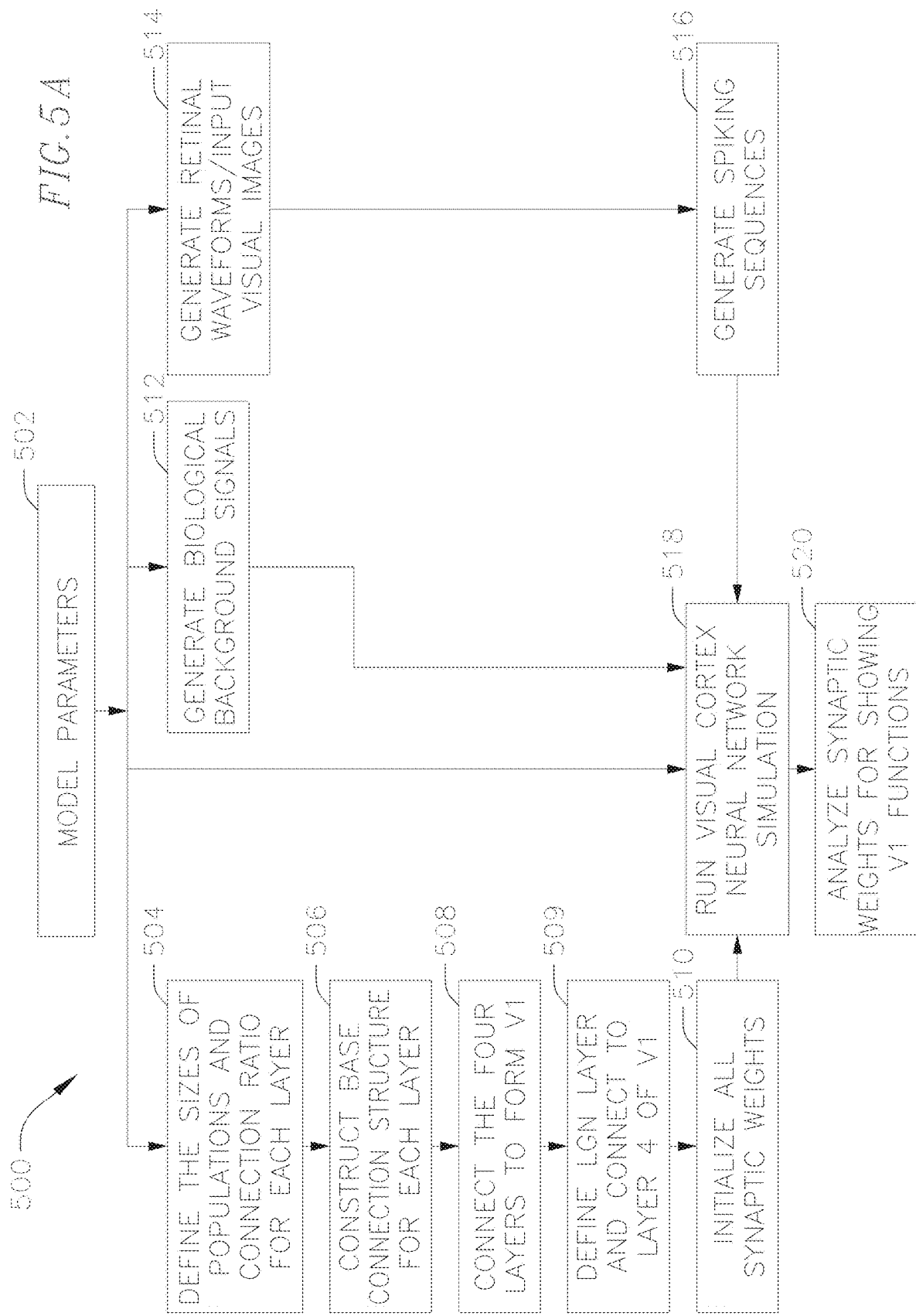
FIG. 5A is a flowchart illustrating a method for emulating a primary visual cortex V1 according to one embodiment of the present invention.

Referring to FIG. 5A, in operation 502, model parameters, such as the numbers of neurons in each of the layers, are supplied to the system. In operation 504 the parameters are used to define sizes of populations of the various layers and connection ratios for each of those layers with layers that the layers are connected to. In operation 506, a base connection structure 200 (e.g., including an excitatory layer 200e and an inhibitory layer 200i) is constructed for each of the four layers (Layer 2/3 202, Layer 4 204, Layer 5 205, and Layer 6 206) by creating the individual neurons and connecting them to one another based on the connection ratios and the connection probabilities described above. In operation 508, the four base connection structures are connected to each other, based on their connection ratios, to form the V1 neural network 300 (e.g., as shown in FIG. 3). Similarly, in operation 509, the neurons of the LGN are connected to the excitatory layer 204e and inhibitory layer 204i of Layer 4. In operation 510, the synaptic weights are all supplied with initial values (e.g., set randomly based on a uniform distribution or set to the same small value). In operation 512, the background random signals are generated to simulate the random background signals present in real biological systems.

In operation 514, visual stimulus signals are generated for the visual cortex emulation. Because the visual cortex neural network takes spiking sequences as input, the visual stimulus signals are converted into spiking sequences in operation 516 before they are fed into the visual cortex network 300 via the input 410 and the LGN layer 420.

In operation 518, the emulation is run, emulating the neuron dynamics and performing the STDP-based synaptic learning based on the defined neural network 300. The emulation results (e.g., the resulting synaptic weights and spiking activities) can be analyzed in operation 520 to show the functionality of the modeled system.

Experimental Results

Emulation of the model was conducted on a neural network according to an embodiment of the present invention. Because ocular dominance maps (ODMs) and synaptic conductance distribution maps (CDMs) are well-studied functionalities of the primary visual cortex V1 of living brains, the biological data were compared to emulation results to measure the quality of the model.

The population sizes of the various layers of the model used in the experiment are shown below in Table 1 (where a size of k×k refers to a two dimensional grid of neurons with k neurons on each side, for a total of $k^2$ neurons, and where "E" refers to an excitatory layer, "I" refers to an inhibitory layer, and the number refers to the layer, where layer "2/3" is abbreviated as "3"):

TABLE 1

Sizes of neuronal populations

| Model Layer | Size |
| --- | --- |
| E3 | 124 × 124 |
| I3 | 66 × 66 |
| E4 | 128 × 128 |
| I4 | 64 × 64 |
| E5 | 60 × 60 |
| I5 | 28 × 28 |
| E6 | 104 × 104 |
| I6 | 47 × 47 |
| LGN | 24 × 24 |

The connection ratios between the layers of the model used in the experiment are shown below in Table 2. The values in each row correspond to the number of connections from each neuron in that row layer to neurons in the column layers. For example, the first row in Table 2 is labeled Layer E3 and that row has a value of "88" in the column for Layer I3. This indicates that each neuron in E3 is uniformly connected to 88 neurons in Layer I3. As another example, the last row in Table 2 is labeled LGN and that row has a value of "235" in the column for Layer E4. This indicates that each neuron in the LGN layer is uniformly connected to 235 neurons of layer E4. In addition, as discussed above, connections within layers (within-layer connections 280) follow a Gaussian distribution and, as such, cells along the diagonal of Table 2, where layers are paired with themselves, have the value "G":

TABLE 2

Neural connection ratio

| | E3 | I3 | E4 | I4 | E5 | I5 | E6 | I6 | LGN |
| --- | --- | --- | --- | --- | --- | --- | --- | --- | --- |
| E3 | G | 88 | 77 | 8 | 103 | 13 | 77 | 2 | |
| I3 | 445 | G | 48 | 5 | 22 | 2 | 18 | 0 | |
| E4 | 141 | 20 | G | 54 | 29 | 3 | 60 | 2 | |
| I4 | 30 | 5 | 338 | G | 11 | 1 | 49 | 0 | |
| E5 | 280 | 40 | 54 | 7 | G | 13 | 151 | 8 | |
| I5 | 30 | 40 | 2 | 5 | 58 | G | 50 | 4 | |
| E6 | 35 | 0 | 475 | 74 | 22 | 2 | G | 18 | |
| I6 | 0 | 0 | 0 | 0 | 0 | 0 | 0 | G | |
| LGN | | | 235 | 74 | | | | | n/a | where "G" stands for a Gaussian distributed connection (e.g., connections between neurons in the same layer).

All of the within-layer-connections are Gaussian-distributed connections (see Equation 6), where the parameters for the Gaussian-distributed connections are shown below in Table 3:

TABLE 3

Parameters for Gaussian-distributed connections

| | A | σ |
| --- | --- | --- |
| E3 | 1.0 | 0.9 |
| I3 | 0.8 | 0.55 |
| E4 | 1.0 | 0.8 |
| I4 | 0.8 | 0.6 |
| E5 | 1.0 | 0.6 |
| I5 | 0.8 | 0.5 |
| E6 | 1.0 | 0.6 |
| I6 | 0.8 | 0.6 |

To produce the conductance distribution maps (CDMs), the four-layer V1 network described above was emulated for one million iterations (or cycles) with background random signals as stimulus signals, where each of the iterations of the emulation corresponded to one millisecond in emulated time. The background random signals were random voltage signals that were randomly injected to 65% of all neurons for 30 iterations (e.g., 30 milliseconds of emulated time). FIGS. 6A-6D are depictions of the conductance distribution maps experimentally obtained from the E-layers of the four layers of the model of V1—Layer 2/3, Layer 4, Layer 5, and Layer 6, respectively—after the completion of the one million iterations of the emulation (e.g., when every iteration corresponds to one millisecond of emulated time, one million iterations corresponds to one thousand seconds of emulated time).

From biological studies, layers E3 and E4 are known to be two major visual information processing regions of V1. The CDMs of layers E3 and E4 generated by the emulation are similar to the CDMs obtained from biological experiments (in particular, noting the distinctive "pinwheel" pattern of the layers, thereby indicating directional sensitivity of the trained model), therefore confirming that the above described model is accurate for modeling the primary visual cortex V1 network.

To verify the ocular dominance maps (ODMs) of the modeled V1 network, Layer 4 of the V1 network 300 was emulated for 4 million iterations (e.g., when every iteration corresponds to one millisecond of emulated time, 4 million iterations corresponds to 4 thousands seconds of emulated time). During the first 2 million iterations, the network stimulus signals were background random signals as described above. During the second 2 million iterations, the network stimulus signals continued to include background random signals and also included retinal waveforms input through the LGN layer.

Figure 7A:
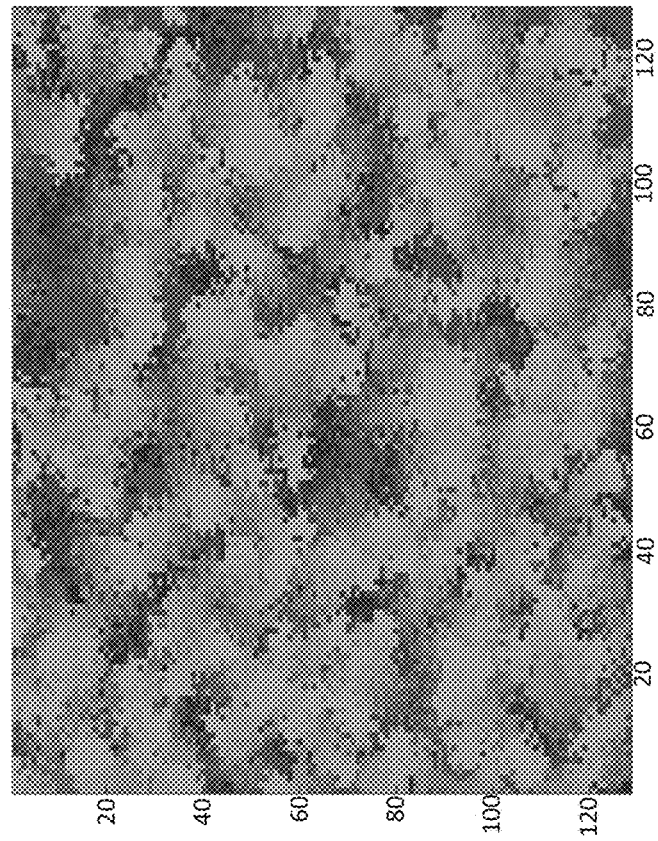
FIGS. 7A-7B show a pair of example retinal waveform images according to one embodiment of the present invention.
Figure 7B:
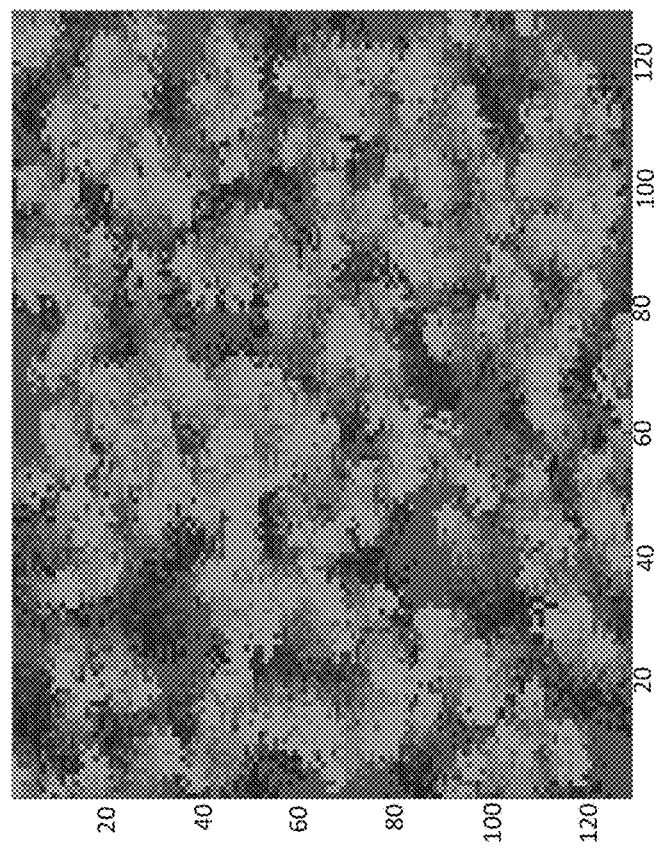

The retinal waveforms supplied to the LGN layer included two sets of waveforms: one set for the left eye and one set for the right eye. The retinal waveforms were generated at random locations in the image planes with linear diffusion rates and propagation duration of 15 iterations of the emulation. In other words, the retinal waveforms are generated by randomly selecting a location on the image plane to generate a signal and then changing the location of the signal at a fixed rate ("linear diffusion rate") for the propagation duration. FIGS. 7A-7B show a pair of example retinal waveform images according to one embodiment of the present invention. While some embodiments of the present invention are trained using the retinal waveforms described above, embodiments of the present invention are not limited thereto, and other types of inputs may be generated and used to train the model instead.

Figures 9A, 9B:
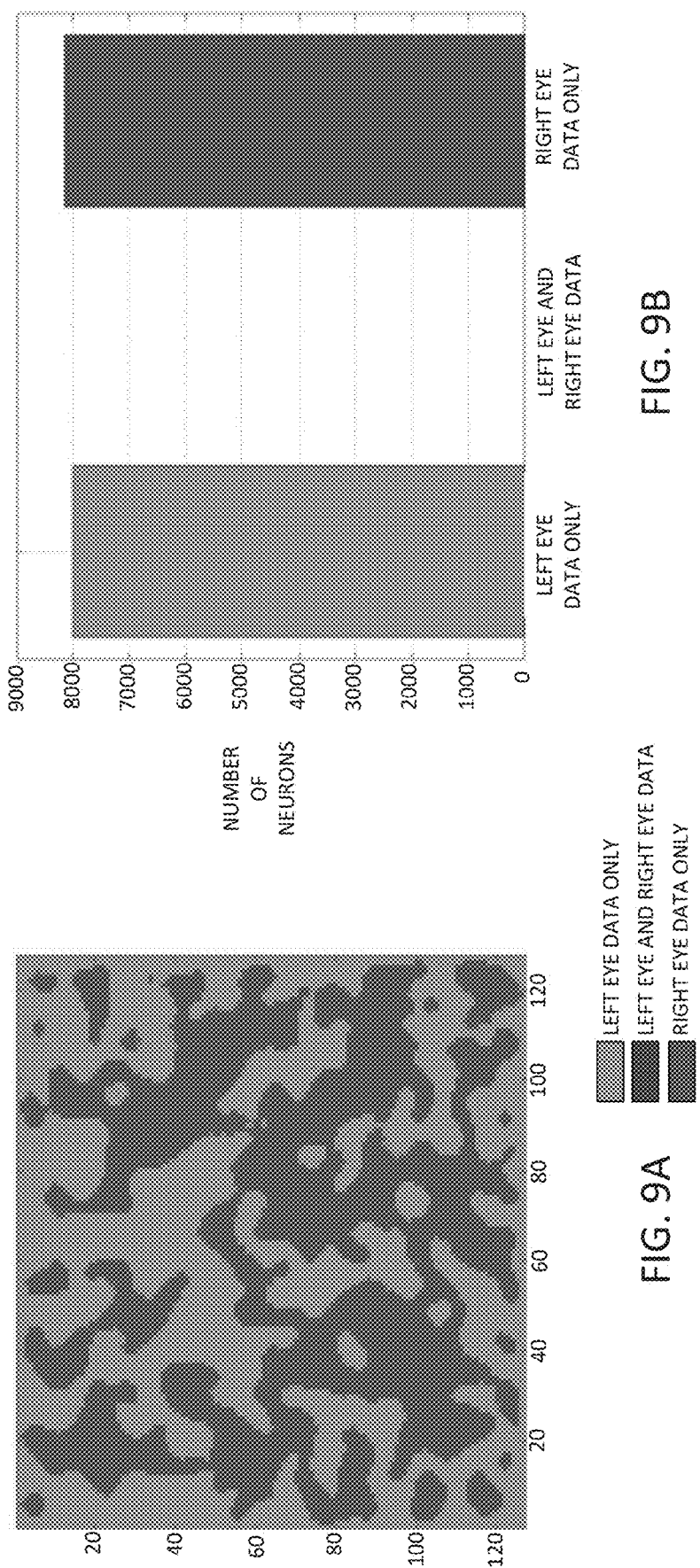
FIG. 9A is an ocular dominance map of a V1 network, after running the training, according to one embodiment of the present invention.
FIG. 9B is a histogram illustrating the ocular dominance of neurons in the V1 network, after running the training, according to one embodiment of the present invention.

After the 4 million iterations of the emulation were completed, an ocular dominance map (ODM) was then measured from the network based on the synaptic weights that connect the LGN neurons and the E4 neurons. FIG. 8A is an initial ODM from LGN to E4 according to one embodiment of the present invention, and FIG. 8B is a histogram showing counts of neurons in the ODM of FIG. 8A that process only left eye data (the green bar on the left), only right eye data (the red bar on the right), or both left eye and right eye (or "binocular") data (the blue bar in the middle). FIG. 9A is the ODM from LGN to E4 after 4 million iterations of the emulation, and FIG. 9B is a histogram showing counts of neurons in the ODM of FIG. 9A. A well-balanced ocular dominance map (a map of strips of neurons responding to only one eye) is a well-known feature of the human visual cortex. Our experimental test shows that our computational model is able to form this feature. As seen in FIGS. 8A-8B, before training, many of the neurons are binocular (shown by the large blue area in the ODM of FIG. 8A and the tall center blue bar in the histogram of FIG. 8B). However, after training, there are no binocular neurons and all of the neurons have been trained to process only left eye or right eye data (shown by the absence of blue area in the ODM of FIG. 9A and the absence of the blue bar in the histogram of FIG. 9B). Therefore, the model of the neural network automatically achieves a well-balanced ODM in the modeled Layer 4, which is in agreement with observed biological studies of Layer 4 of the primary visual cortex V1, where the biological neurons are dedicated to processing information from the left eye or the right eye, but not both the left and right eyes.

Deployment of a Model in a Working System

Figure 5B:
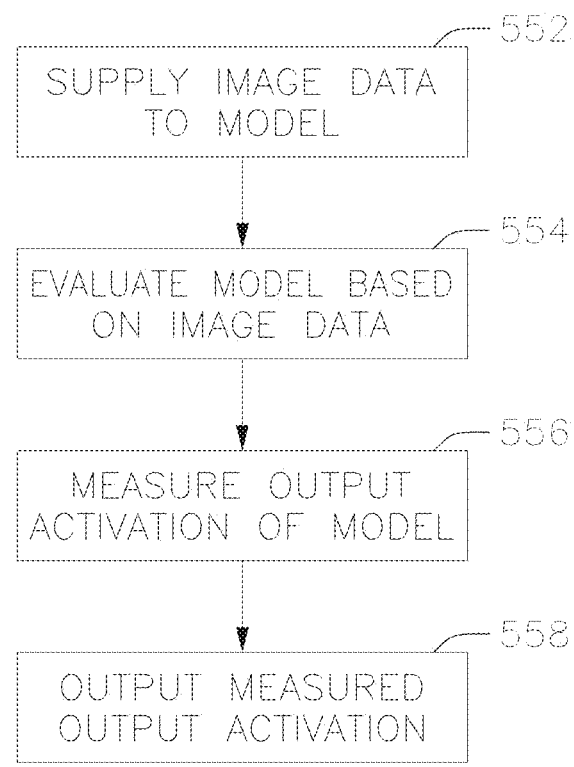
FIG. 5B is a flowchart illustrating a method for detecting a feature in image data according to one embodiment of the present invention.

After confirming the efficacy of a trained model, the trained network 300, including the trained synaptic weights, can be deployed in a running processor such as the neuromorphic hardware described above. FIG. 5B is a flowchart illustrating a method 550 for detecting a feature in image data according to one embodiment of the present invention. Referring to FIG. 5B, in operation 552, this deployed running system may be supplied with image data (e.g., image data captured from one or more image sensors) to process and to identify features in the captured image data in real time. These features may include, for example, edges (regions containing high contrast), man-made objects, and moving objects. These features may include information about the size, motion, and orientation of visual objects, and may be measured from the output activation of the layers of the model. In operation 554, the trained network 300 can be evaluated in accordance with the input data (e.g., supplying the input data to the LGN layer 420, and iteratively propagating signals between the neurons of the inhibitory and excitatory neurons of Layer 4, Layer 2/3, Layer 5, and Layer 6 in accordance with the within-layer and between-layer connections).

In operation 556, the output activation of the neurons may be measured. The output activation of the model network may include, for example, outputs of a plurality of neurons where each output neuron corresponds to a location or region of the input image data and indicates the presence or absence of the feature in corresponding region of the input image data (e.g., as reflected in the conductance distribution map or CDM). As a more concrete example, in a model network that is trained to detect edges (e.g., high contrast regions) in the input images, the output activation may include a plurality of larger valued outputs in regions where the model network detects high contrast (e.g., large differences in the values of the pixels in the corresponding regions) in the input data and lower valued outputs where the model network detects low contrast (e.g., small differences on no differences in the values of the pixels in the corresponding regions). The output activation of the modeled V1 network may be supplied in operation 558 to another program or another processor (e.g., a conventional processor) for further processing of the detected features, e.g., for performing object recognition based on the detected features. The output activation of the modeled V1 network may also be supplied to a user interface for display to a user, in order to alert the user of the detected features in the image data. For example, the user interface may display the images captured by the one or more image sensors and use the output activation of the modeled V1 network to identify portions of the captured image that can be overlaid or composited with highlights or boxes outlining the detected features. As another example, the output activation of the modeled V1 network in response to the input image may be displayed on the graphical user interface to provide indications of the locations of detected features. As yet another example, the output activation may be supplied to a tracking system that controls a device (e.g., a camera system that includes the one or more image sensors) in accordance with the output activation (e.g., based on the location of the detected feature).

As such, embodiments of the present invention are directed to methods for modeling the behavior of the primary visual cortex V1. Experimental results show that the model described above exhibits behavior that effectively emulates the behavior observed in biological studies of a natural primary visual cortex V1. Therefore, embodiments of the present invention may provide systems and models that can be applied to improve computer vision systems.

The model 300 of the visual perception area may be implemented with logic gates as illustrated, or with any other embodiment of a processor. The term "processor" is used herein to include any combination of hardware, firmware, and software, employed to process data or digital signals. Processing unit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). For example, as described above, a neuromorphic chip is a form of a special purpose processing unit that can be used to implement embodiments of the present invention.

Figure 10A:
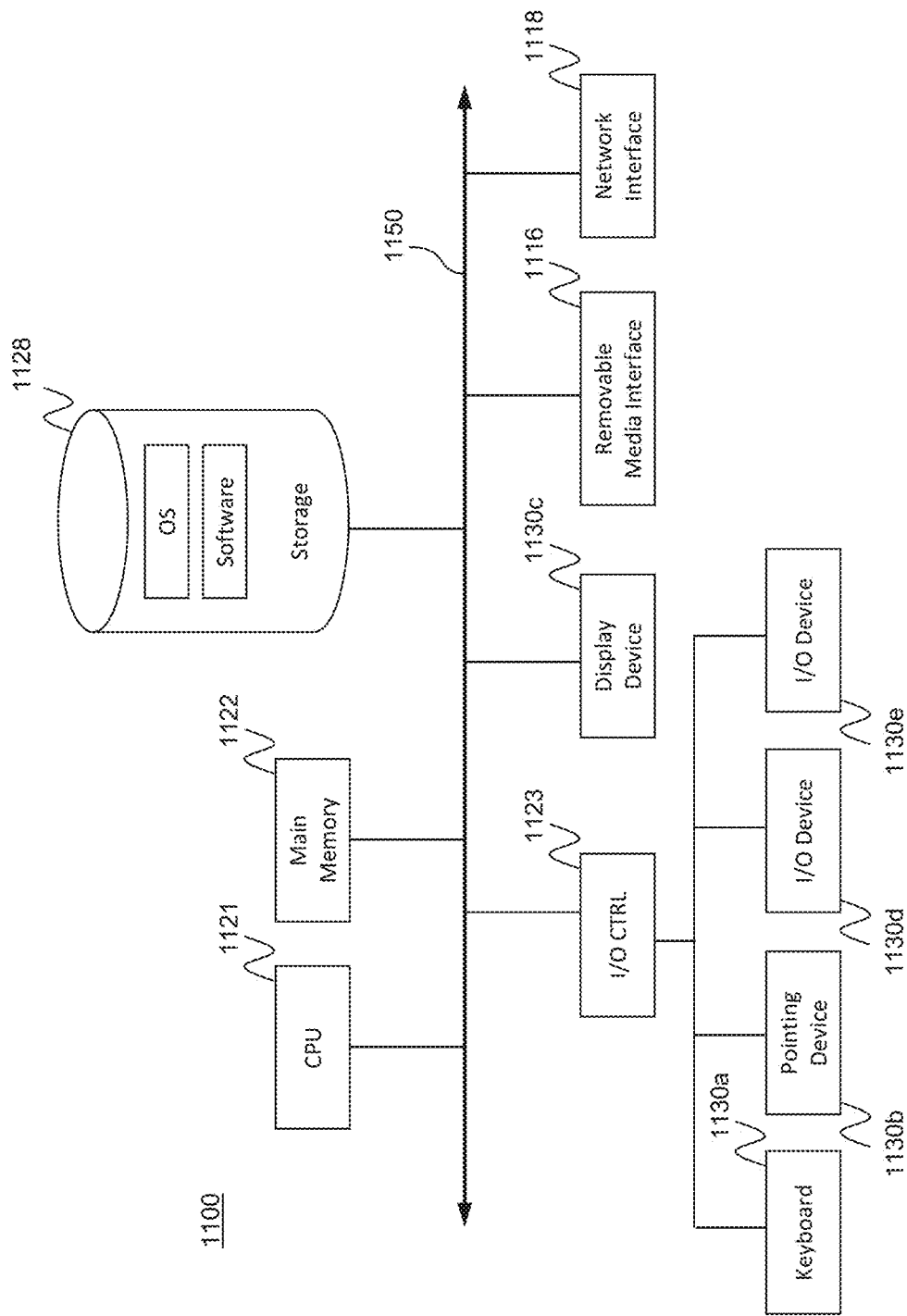
FIG. 10A is a block diagram of a computing device according to an embodiment of the present invention.
Figure 10B:
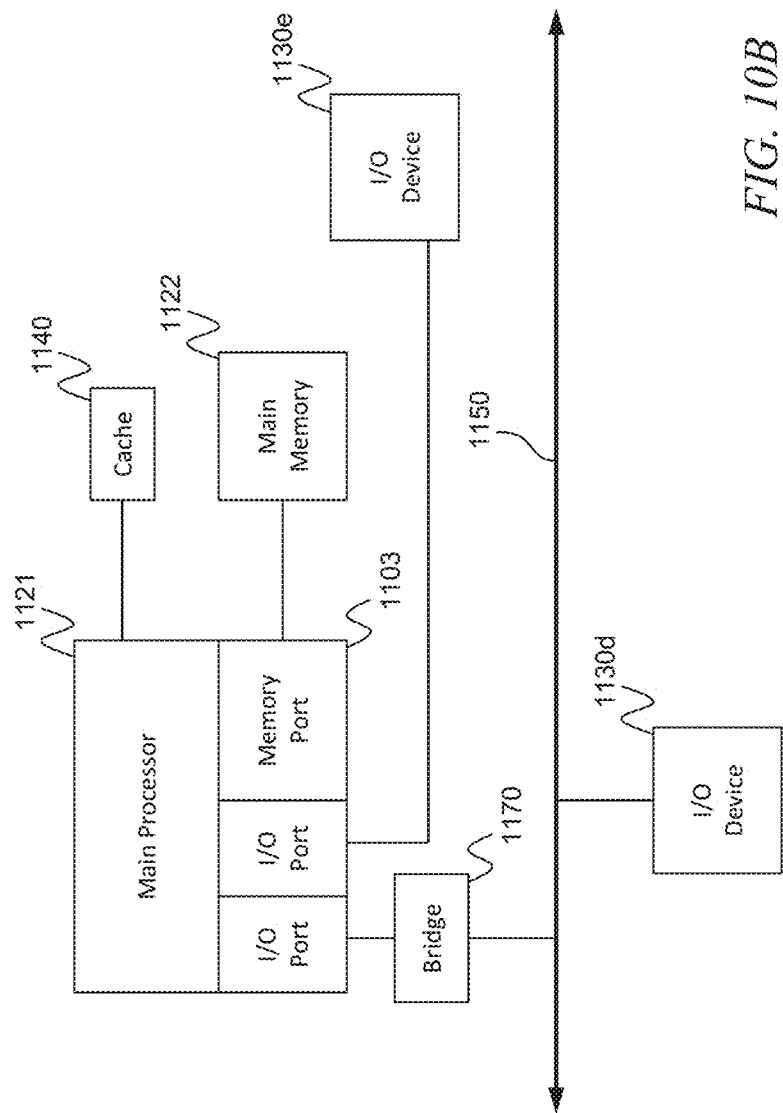
FIG. 10B is a block diagram of a computing device according to an embodiment of the present invention.

In one embodiment the methods are run on one or more computing devices 1100, such as that illustrated in FIGS. 10A-10B. FIGS. 10A-10B depict block diagrams of a computing device 1100 as may be employed in exemplary embodiments of the present invention. As shown in FIG. 10A and FIG. 10B, each computing device 1100 includes a central processing unit 1121, and a main memory unit 1122. As shown in FIG. 10A, a computing device 1100 may include a storage device 1128, a removable media interface 1116, a network interface 1118, an input/output (I/O) controller 1123, one or more display devices 1130c, a keyboard 1130a and a pointing device 1130b, such as a mouse. The storage device 1128 may include, without limitation, storage for an operating system and software. As shown in FIG. 10B, each computing device 1100 may also include additional optional elements, such as a memory port 1103, a bridge 1170, one or more additional input/output devices 1130d, 1130e and a cache memory 1140 in communication with the central processing unit 1121. Input/output devices, e.g., 1130a, 1130b, 1130d, and 1130e, may be referred to herein using reference numeral 1130.

The central processing unit 1121 is any logic circuitry that responds to and processes instructions fetched from the main memory unit 1122. It may be implemented, for example, in an integrated circuit, in the form of a microprocessor, microcontroller, or graphics processing unit (GPU), or in a field-programmable gate array (FPGA) or application-specific integrated circuit (ASIC). Main memory unit 1122 may be one or more memory chips capable of storing data and allowing any storage location to be directly accessed by the central processing unit 1121. In the embodiment shown in FIG. 10A, the central processing unit 1121 communicates with main memory 1122 via a system bus 1150. FIG. 10B depicts an embodiment of a computing device 1100 in which the central processing unit 1121 communicates directly with main memory 1122 via a memory port 1103.

FIG. 10B depicts an embodiment in which the central processing unit 1121 communicates directly with cache memory 1140 via a secondary bus, sometimes referred to as a backside bus. In other embodiments, the central processing unit 1121 communicates with cache memory 1140 using the system bus 1150. Cache memory 1140 typically has a faster response time than main memory 1122. In the embodiment shown in FIG. 10A, the central processing unit 1121 communicates with various I/O devices 1130 via a local system bus 1150. Various buses may be used as a local system bus 1150, including a Video Electronics Standards Association (VESA) Local bus (VLB), an Industry Standard Architecture (ISA) bus, an Extended Industry Standard Architecture (EISA) bus, a MicroChannel Architecture (MCA) bus, a Peripheral Component Interconnect (PCI) bus, a PCI Extended (PCI-X) bus, a PCI-Express bus, or a NuBus. For embodiments in which an I/O device is a display device 1130c, the central processing unit 1121 may communicate with the display device 1130c through an Advanced Graphics Port (AGP). FIG. 10B depicts an embodiment of a computer 1100 in which the central processing unit 1121 communicates directly with I/O device 1130e. FIG. 10B also depicts an embodiment in which local busses and direct communication are mixed: the central processing unit 1121 communicates with I/O device 1130d using a local system bus 1150 while communicating with I/O device 1130e directly.

A wide variety of I/O devices 1130 may be present in the computing device 1100. Input devices include one or more keyboards 1130a, mice, trackpads, trackballs, microphones, and drawing tablets. Output devices include video display devices 1130c, speakers, and printers. An I/O controller 1123, as shown in FIG. 10A, may control the I/O devices. The I/O controller may control one or more I/O devices such as a keyboard 1130a and a pointing device 1130b, e.g., a mouse or optical pen.

Referring again to FIG. 10A, the computing device 1100 may support one or more removable media interfaces 1116, such as a floppy disk drive, a CD-ROM drive, a DVD-ROM drive, tape drives of various formats, a USB port, a Secure Digital or COMPACT FLASH™ memory card port, or any other device suitable for reading data from read-only media, or for reading data from, or writing data to, read-write media. An I/O device 1130 may be a bridge between the system bus 1150 and a removable media interface 1116.

The removable media interface 1116 may for example be used for installing software and programs. The computing device 1100 may further comprise a storage device 1128, such as one or more hard disk drives or hard disk drive arrays, for storing an operating system and other related software, and for storing application software programs. Optionally, a removable media interface 1116 may also be used as the storage device. For example, the operating system and the software may be run from a bootable medium, for example, a bootable CD.

In some embodiments, the computing device 1100 may comprise or be connected to multiple display devices 1130c, which each may be of the same or different type and/or form. As such, any of the I/O devices 1130 and/or the I/O controller 1123 may comprise any type and/or form of suitable hardware, software, or combination of hardware and software to support, enable or provide for the connection to, and use of, multiple display devices 1130c by the computing device 1100. For example, the computing device 1100 may include any type and/or form of video adapter, video card, driver, and/or library to interface, communicate, connect, or otherwise use the display devices 1130c. In one embodiment, a video adapter may comprise multiple connectors to interface to multiple display devices 1130c. In other embodiments, the computing device 1100 may include multiple video adapters, with each video adapter connected to one or more of the display devices 1130c. In some embodiments, any portion of the operating system of the computing device 1100 may be configured for using multiple display devices 1130c. In other embodiments, one or more of the display devices 1130c may be provided by one or more other computing devices, connected, for example, to the computing device 1100 via a network. These embodiments may include any type of software designed and constructed to use the display device of another computing device as a second display device 1130c for the computing device 1100. One of ordinary skill in the art will recognize and appreciate the various ways and embodiments that a computing device 1100 may be configured to have multiple display devices 1130c.

A computing device 1100 of the sort depicted in FIG. 10A and FIG. 10B may operate under the control of an operating system, which controls scheduling of tasks and access to system resources. The computing device 1100 may be running any operating system, any embedded operating system, any real-time operating system, any open source operating system, any proprietary operating system, any operating systems for mobile computing devices, or any other operating system capable of running on the computing device and performing the operations described herein.

The computing device 1100 may be any workstation, desktop computer, laptop or notebook computer, server machine, handheld computer, mobile telephone or other portable telecommunication device, media playing device, gaming system, mobile computing device, or any other type and/or form of computing, telecommunications or media device that is capable of communication and that has sufficient processor power and memory capacity to perform the operations described herein. In some embodiments, the computing device 1100 may have different processors, operating systems, and input devices consistent with the device.

In other embodiments the computing device 1100 is a mobile device, such as a Java-enabled cellular telephone or personal digital assistant (PDA), a smart phone, a digital audio player, or a portable media player. In some embodiments, the computing device 1100 comprises a combination of devices, such as a mobile phone combined with a digital audio player or portable media player.

While the present invention has been described in connection with certain exemplary embodiments, it is to be understood that the invention is not limited to the disclosed embodiments, but, on the contrary, is intended to cover various modifications and equivalent arrangements included within the spirit and scope of the appended claims, and equivalents thereof.

What is claimed is:

1. A method for emulating a primary visual cortex using a model, the model comprising:
    four layers comprising: a supragranular layer, a granular layer, a first infragranular layer, and a second infragranular layer, each of the four layers comprising a base connection structure, the base connection structure comprising a plurality of layers including:
        an excitatory layer comprising a plurality of excitatory neurons arranged in a two dimensional grid; and
        an inhibitory layer comprising a plurality of inhibitory neurons arranged in a two dimensional grid;
    a plurality of within-layer connections between the neurons of each layer, the probability of a first neuron of the layer being connected to a second neuron of the same layer being a function of the distance between the first neuron and the second neuron in accordance with a Gaussian distribution;
    a plurality of between-layer connections between the neurons of different layers, the probability of a neuron of a first layer of the different layers being connected to a neuron of a second layer of the different layers being in accordance with a uniform distribution; and
    a plurality of input connections from a plurality of lateral geniculate nucleus (LGN) neurons of an input LGN layer to the excitatory layer and the inhibitory layer of the granular layer, the between-layer connections comprising connections from the excitatory layer of the granular layer to the inhibitory layer of the granular layer, the probability of an LGN neuron being connected to a neuron of the granular layer being in accordance with a uniform distribution, the method comprising:
    supplying, by a processor, an input signal from an image sensor to the LGN neurons;
    measuring, by the processor, an output activation of neurons in the four layers to detect the presence of at least one feature in the input signal; and
    outputting, by the processor, the detection of the presence of the at least one feature based on the output activation of neurons in the four layers.

2. The method of claim 1, wherein a plurality of model parameters comprise a plurality of connection ratios, each of the connection ratios corresponding to the uniform distribution associated with a plurality of between-layer connections between a first layer of the different layers to a second layer of the different layers.

3. The method of claim 1, wherein a plurality of model parameters comprise a plurality of Gaussian distribution parameters A and a for each of the plurality of layers,
    wherein the first neuron of the layer is located at coordinates ($x_0$, $y_0$) within the layer and the second neuron of the layer is located at coordinates (x, y) within the layer, and
    wherein the probability P that the first neuron is connected to the second neuron is:

$$P(x, y) = A * e^{\frac{-[(x-x_0)^2 + (y-y_0)^2]}{2\sigma}}.$$

4. The method of claim 1, wherein a plurality of model parameters comprise a plurality of neuron populations, wherein each of the neuron populations corresponds to a number of neurons in a corresponding one of the layers.

5. The method of claim 1, wherein the model is trained by:
    setting a plurality of initial synaptic weights, each of the initial synaptic weights corresponding to one of the connections;
    generating visual stimulus signals;
    supplying the visual stimulus signals to the LGN neurons; and
    updating the synaptic weights of the connections by iteratively:
        computing propagating signals through the connections in accordance with the synaptic weights;
        determining whether each neuron releases a signal in accordance with an accumulated signal;
        determining a plurality of timings of the signals released by the neurons; and
        computing new synaptic weights in accordance with the timings and spike timing dependent plasticity synaptic learning.

6. The method of claim 5, wherein the model is further trained by supplying a plurality of background random signals to the neurons.

7. The method of claim 5, wherein the generating the visual stimulus signals comprises generating a plurality of spiking sequences.

8. The method of claim 5, further comprising analyzing the synaptic weights to generate an ocular dominance map and a synaptic conductance distribution map.

9. The method of claim 5, wherein the visual stimulus signals comprise a plurality of left visual stimulus signals and a plurality of right visual stimulus signals, wherein the LGN neurons comprise a plurality of left LGN neurons configured to receive the left visual stimulus signals and plurality of right visual stimulus neurons configured to receive the right visual stimulus signals, and wherein each of the neurons in the excitatory layer of a granular layer is connected with non-zero synaptic weight to only left LGN neurons or to only right LGN neurons.

10. The method of claim 1, wherein the processor is a neuromorphic chip.

11. A system configured to detect a feature in an input image, the system comprising a processor configured to evaluate a model, the model being configured based on a plurality of model parameters, the model including:
   four layers comprising: a supragranular layer, a granular layer, a first infragranular layer, and a second infragranular layer, each of the four layers comprising a base connection structure, the base connection structure comprising a plurality of layers including:
      an excitatory layer comprising a plurality of excitatory neurons arranged in a two dimensional grid; and
      an inhibitory layer comprising a plurality of inhibitory neurons arranged in a two dimensional grid;
   a plurality of within-layer connections between the neurons of each layer, the probability of a first neuron of the layer being connected to a second neuron of the same layer being a function of the distance between the first neuron and the second neuron in accordance with a Gaussian distribution;
   a plurality of between-layer connections between the neurons of different layers, the probability of a neuron of a first layer of the different layers being connected to a neuron of a second layer of the different layers being in accordance with a uniform distribution; and
   a plurality of input connections from a plurality of lateral geniculate nucleus (LGN) neurons of an input LGN layer to the excitatory layer and the inhibitory layer of the granular layer, the between-layer connections comprising connections from the excitatory layer of the granular layer to the inhibitory layer of the granular layer, the probability of an LGN neuron being connected to a neuron of the granular layer being in accordance with a uniform distribution;
   the system being configured to:
      receive input image data from an image sensor;
      supply the input image data to the LGN neurons of the model;
      compute an activation output of the model; and
      generate user feedback in accordance with the activation output of the model, the user feedback indicating the presence of the feature in the input data.

12. The system of claim 11, wherein the model parameters comprise a plurality of connection ratios, each of the connection ratios corresponding to the uniform distribution associated with a plurality of between-layer connections between a first layer of the different layers to a second layer of the different layers.

13. The system of claim 11, wherein the model parameters comprise a plurality of Gaussian distribution parameters A and a for each of the plurality of layers,
   wherein the first neuron of the layer is located at coordinates $(x_0, y_0)$ within the layer and the second neuron of the layer is located at coordinates $(x, y)$ within the layer, and wherein the probability P that the first neuron is connected to the second neuron is:

$$P(x, y) = A * e^{\frac{-[(x-x_0)^2 + (y-y_0)^2]}{2\sigma}}.$$

14. The system of claim 11, wherein the model parameters comprise a plurality of neuron populations, wherein each of the neuron populations corresponds to a number of neurons in a corresponding one of the layers.

15. The system of claim 11, wherein the model parameters further comprise a plurality of initial synaptic weights, each of the initial synaptic weights corresponding to one of the connections, and
   wherein the processor is configured to train the model by:
      receiving visual stimulus signals;
      supplying the visual stimulus signals to the LGN neurons; and
      updating the synaptic weights of the connections by iteratively:
         computing propagating signals through the connections in accordance with the synaptic weights;
         determining whether each neuron releases a signal in accordance with an accumulated signal;
         determining a plurality of timings of the signals released by the neurons; and
         computing new synaptic weights in accordance with the timings and spike timing dependent plasticity synaptic learning.

16. The system of claim 15, wherein the processor is further configured to train the model by supplying a plurality of background random signals to the neurons.

17. The system of claim 15, wherein the visual stimulus signals comprise a plurality of left visual stimulus signals and a plurality of right visual stimulus signals,
   wherein the LGN neurons comprise a plurality of left LGN neurons configured to receive the left visual stimulus signals and plurality of right visual stimulus neurons configured to receive the right visual stimulus signals, and
   wherein each of the neurons in the excitatory layer of a granular layer is connected with non-zero synaptic weight to only left LGN neurons or to only right LGN neurons.

18. The system of claim 11, wherein the processor is a neuromorphic chip.

19. A non-transitory computer readable medium having instructions stored thereon that, when executed by a processor, cause the processor to:
   evaluate a model of a primary visual cortex, the model comprising:
      four layers comprising: a supragranular layer, a granular layer, a first infragranular layer, and a second infragranular layer, each of the four layers comprising a base connection structure, the base connection structure comprising a plurality of layers including:
         an excitatory layer comprising a plurality of excitatory neurons arranged in a two dimensional grid; and
         an inhibitory layer comprising a plurality of inhibitory neurons arranged in a two dimensional grid;
      a plurality of within-layer connections between the neurons of each layer, the probability of a first neuron of the layer being connected to a second neuron of the same layer being a function of the distance between the first neuron and the second neuron in accordance with a Gaussian distribution;

a plurality of between-layer connections between the neurons of different layers, the probability of a neuron of a first layer of the different layers being connected to a neuron of a second layer of the different layers being in accordance with a uniform distribution; and a plurality of input connections from a plurality of a lateral geniculate nucleus (LGN) neurons of an input LGN layer to the excitatory layer and the inhibitory layer of the granular layer, the between-layer connections comprising connections from the excitatory layer of the granular layer to the inhibitory layer of the granular layer, the probability of an LGN neuron being connected to a neuron of the granular layer being in accordance with a uniform distribution;

supply an input signal from an image sensor to the LGN neurons;

measure an output activation of neurons in the four layers to detect the presence of at least one feature in the input signal; and output the detection of the presence of the at least one feature based on the output activation of neurons in the four layers.

* * * * *